United States Patent [19]

Takaku et al.

[11] Patent Number: 5,114,710

[45] Date of Patent: May 19, 1992

[54] M-CSF AS A THERAPEUTIC AGENT FOR THROMBOCYTOPENIA

[75] Inventors: Fumimaro Takaku, Tokyo; Kazuo Motoyoshi, Saitama, both of Japan

[73] Assignees: Green Cross Corporation, Osaka; Morinaga Milk Industry Co., Ltd., Tokyo, both of Japan

[21] Appl. No.: 308,593

[22] Filed: Feb. 10, 1989

[30] Foreign Application Priority Data

Feb. 10, 1988 [JP] Japan .................................. 63-29819

[51] Int. Cl.$^5$ ................................................ A61K 37/02
[52] U.S. Cl. ........................................ 424/85.1; 514/2; 514/8; 514/12; 514/21
[58] Field of Search ................ 424/85.1; 514/2, 8, 514/12, 21

[56] References Cited

U.S. PATENT DOCUMENTS 4,230,697 10/1980 Nishida et al. .
4,275,056 6/1981 Takaku et al. .

FOREIGN PATENT DOCUMENTS 0212501 8/1986 European Pat. Off. .
0276551 12/1987 European Pat. Off. .
8604587 8/1986 World Int. Prop. O. .

OTHER PUBLICATIONS

Cerretti et al, *Molecular Immunology*, vol. 25 (8) 1988, pp. 761-770.
McDonald et al, CA vol. 111, 1989, #117771k.
Anderson et al, CA vol. 110, 1989, #190839r.
Kuriya et al, CA vol. 106, 1986, #65243h.
Biological Abstracts, vol. 85, No. 6, 1988, p. AB-841, Abstract No. 60968.
Chemical Abstracts, vol. 107, No. 13, Sep. 13, 1987, p. 500, Abstract No. 114079r.

*Primary Examiner*—Garnette D. Draper
*Attorney, Agent, or Firm*—Sughrue, Mion, Zinn Macpeak & Seas

[57] ABSTRACT

A therapeutic agent for thrombocytopenia due to hemopoietic disorder induced by various causes comprises as an active ingredient a specific human monocytemacrophage colony stimulating factor. It is administered for the treatment and/or prevention of such thrombocytopenia.

6 Claims, 2 Drawing Sheets

M-CSF AS A THERAPEUTIC AGENT FOR THROMBOCYTOPENIA

FIELD OF THE INVENTION

This invention relates to a therapeutic agent for thrombocytopenia due to hemopoietic disorder induced by various causes. More particularly, the invention relates to a therapeutic agent for thrombocytopenia which comprises a human monocyte-macrophage colony stimulating factor, which is one of human hemopoietic factors, as an active ingredient.

BACKGROUND OF THE INVENTION

Platelet transfusion is a powerful means for treating patients either actually suffering from or facing a high risk of severe hemorrhage due to marked decrease in the number of platelets or decreased hemopoietic function caused by various types of hemopoietic disorder. However, from the medical practice viewpoint, the current situation is not such that platelet preparations are available promptly in sufficient quantities. Moreover, the risk of patients being infected with such pathogenic viruses as ATL (adult T cell leukemia) or AIDS (acquired immune deficiency syndrome) on the occasion of platelet transfusion is remarkably high.

SUMMARY OF THE INVENTION

As a result of investigations made in an attempt to find out a means of promoting platelet formation in patients suffering from or facing a high risk of severe hemorrhage in the course of chemotherapeutic or radiotherapeutic treatment of leukemia or malignant tumor, or suffering from aplastic anemia, the present inventors found that administration of a preparation comprising a specific human monocyte-macrophage colony stimulating factor (CSF) as an active ingredient in the course of chemotherapy can result in rapid restoration of a normal platelet level and have now completed the present invention based on this finding. The instant invention provides a therapeutic agent for thrombocytopenia which is to be administered for the treatment and/or prevention of hemopoietic disorder-induced thrombocytopenia, said agent comprising as an active ingredient a human monocytemacrophage colony stimulating factor wherein said human monocytemacrophage colony stimulating factor has the following physicochemical properties a) to f):

a) Molecular weight

It is a homodimer composed of two identical subunits and, when determined by sodium dodecyl sulfate-polyacrylamide gel electrophoresis (SDS-PAGE), the molecular weight of each subunit resulting from dissociation with a reducing agent is 35,000-45,000 daltons, b) Isoelectric point The isoelectric point (pI) as determined by polyacrylamide gel isoelectric focusing and sucrose density gradient isoelectric focusing techniques is 3.1-3.7, c) Sugar chain-constituting monosaccharides The following sugar chain-constituting monosaccharides have been identified by high-performance liquid chromatography following hydrolysis as being bound to each subunit: mannose, galactose, N-acetylglucosamine, N-acetylgalatosamine and N-acetylneuraminic acid, d) Circular dichroism spectrum The far ultraviolet CD spectrum recorded with a circular dichroism dispersion meter has minimum peaks at the wavelengths 208 and 222 nm, whereby the stimulating factor comprises an α-helix structure, e) Thermal stability The biological activity is not lost even upon heating at 60±0.5° C. for 60 minutes, and f) Infrared absorption spectrum as recorded for the form of a lyophilized powder by the transmission method using a Fouriertransform infrared spectrophotometer is as shown in FIG. 3.

BRIEF DESCRIPTION OF THE DRAWINGS

In the accompanying drawings,

In FIG. 1,

Figure 1:
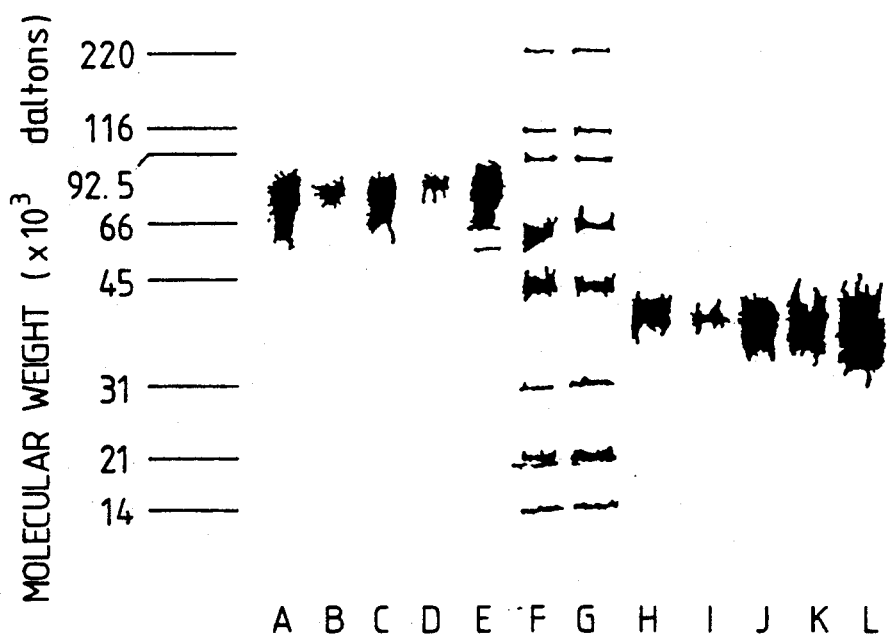
FIG. 1 is an electrophoretic pattern of the CSF according to the invention as obtained in sodium dodecyl sulfate-polyacrylamide gel electrophoresis (SDS-PAGE)

A to E . . . Unreduced substance (dimer)

F to G . . . Molecular weight marker proteins

H to L . . . Reduced substance (subunit).

DETAILED DESCRIPTION OF THE INVENTION

The colony stimulating factor (hereinafter referred to as "CSF"), which is glycoprotein, to be used as the essential active ingredient of the therapeutic agent according to the invention is described in EP-A-276 551 (European patent application filed by one of the Assignees in the instant application). It has colony stimulating activity against mammalian monocytemacrophage series cells, and can be produced in the following manner.

Urine of the healthy human origin is adjusted to pH 8.0-9.0, whereby viscous substances are precipitated and removed. The supernatant is concentrated and desalted using an ultrafiltration membrane allowing the passage of substances having a molecular weight of 10,000-50,000 daltons.

After at least 200-fold concentration (at least 1% (w/v) in terms of protein concentration), the concentrate is adjusted to pH 6.5-7.5 and heat-treated at 60° C. for 10 hours (for inactivation of viruses, etc.). The resulting precipitate is removed by centrifugation and, then the active component is caused to be adsorbed an anion exchanger, for example DEAE-cellulose.

Said ion exchanger is washed with 0.05-0.1 M buffer (pH 6.5-7.5) and, then the active component is eluted with 0.2-0.4 M buffer (pH 6.5-7.5). If necessary, the eluate is concentrated with an ultrafiltration membrane. The eluate is subjected to gel filtration using a gel filtration medium, such as Sephacryl ® S-300 (Pharmacia), equilibrated with a buffer (pH 6.5-7.5) containing a salt, such as ammonium sulfate or sodium chloride, in a concentration of 1-4 M, and a fraction having the molecular weight range of 70,000-150,000 daltons is recovered. Then, said fraction is subjected to treatment for adsorption on a hydrophobic substance having affinity for CSF, for example on Phenyl-Sepharose ® (Pharmacia). Elution is carried out with a buffer (pH 6.5-7.5) containing a salt in a concentration of 0.5-1.0 M. The eluate is concentrated with an ultrafiltration membrane and subjected to gel filtration using a high-speed liquid gel filtration column, such as TSKG-3000SW (Tosoh Corporation), and a fraction having the molecular weight range of 70,000-150,000 daltons is recovered. Said fraction is again concentrated and subjected to treatment by adsorption on a reversed-phase high-performance liquid chromatography column, such as Hi-Pore® RP-304 (Bio-Rad), equilibrated with 0.1% trifluoroacetic acid (TFA) solution (pH 1-2). Elution is carried out with a solvent, such as acetonitrile or isopropyl alcohol, containing 0.1% TFA by the linear concentration gradient elution technique. The thus-obtained CSF is a pure substance having a specific activity of at least $1 \times 10^8$ units per milligram of protein.

The CSF according to the present invention can also be produced by isolating from the culture medium of an M-CSF-producing cell line or M-CSF-producing cells having inserted therein DNA encoding an M-CSF gene by means of recombinant DNA technique.

The thus-produced CSF according to the invention can be purified by utilizing the reaction of the CSF with a specific antibody.

This production method consists of three steps, which are described one by one in the following. [1] Preparation of specific antibody to the colony stimulating glycoprotein (hereinafter referred to as "anti-CSF antibody")

The CSF according to the invention as obtained by the above-mentioned first production method or a modification thereof is used to immunize mammals, for example rabbits, goats, sheep or horses. Thus, the CSF according to the invention is dissolved in physiological saline in a concentration of 0.1-1.0 mg/ml, the solution is admixed with the equal volume of complete Freund's adjuvant, and the mixture is administered subcutaneously to mammals one or two times per week for 4-8 weeks. When the thus-immunized animals show an increased blood antibody titer, a booster dose is given to them by intravenous or subcutaneous injection and, 3-7 days thereafter, blood collection is performed and an antiserum to CSF is separated. The antibody titer of the thus-obtained antiserum against CSF is measured by the test to be mentioned later herein which consists in neutralization of the biological potency of CSF. It is desirable to select those antisera which have an anti-CSF antibody titer such that each milliliter thereof can neutralize at least $5 \times 10^6$ units of the biological potency of CSF. The antiserum collected is purified by two repetitions of salting out with ammonium sulfate followed by DEAE-cellulose chromatography or the like to give the anti-CSF antibody as an immunoglobulin G or M fraction. If necessary, the anti-CSF antibody is further purified by applying it to an antigen column containing as the ligand the CSF or an impurity protein cross-reactive with the anti-CSF antibody as a ligand to thereby cause the anti-CSF antibody alone to be adsorbed on said column or by causing impurity proteins to be adsorbed on an appropriate column. [2] Preparation of antibody-bound carrier Any of known insoluble carriers capable of forming a chemical bond with the $NH_2$— or COOH— group of the antibody protein can be used as the insoluble carrier for binding the anti-CSF antibody. For example, there may be mentioned cyanogen bromide-activated or epoxidized polysaccharide gels, formylated polysaccharide gels, and aminoethylated or hydrazidized polymers. In carrying out the binding reaction between the insoluble carrier and the anti-CSF antibody, the antibody solution should be adjusted to make the same optimal for said reaction, since the optimal reaction conditions may vary according to the binding group of the insoluble carrier selected. For example, the antibody should be dissolved in a carbonate buffer having a pH of 8-10 in the case of cyanogen bromide carrier, in a solution having a pH of at least 10 in the case of epoxidized carriers, and in a neutral solution in the case of formylated carriers. The temperature conditions to be employed for said binding reaction also may vary depending on the insoluble carrier. Generally, however, the binding reaction for the practice of the invention is desirably carried out at a low temperature not exceeding 25° C. In particular, in the case of cyanogen bromide-activated carriers, the reaction should be carried out at 4° C. or below. The antibody quantity to be bound is generally 10-50 mg, preferably 20-30 mg, per gram (wet weight) of the insoluble carrier, and the antibody concentration in carrying out the binding reaction is adjusted to 1-4% (w/v). After completion of the binding reaction, those reactive groups remaining on the carrier without binding the antibody are inactivated by an appropriate treatment method, whereby the desired antibody-bound carrier is obtained. [3] CSF purification with antibody-bound carrier The antibody-bound carrier is washed with a buffer of pH 6-8 containing a salt, such as sodium chloride, in a concentration of 0.5-1.0 M. The thus-washed antibody-bound carrier is packed into a column or suspended in a buffer. The former is used for column chromatography and the latter for batchwise chromatography. The solution which contains the CSF according to the invention and is to be purified is, for example, a human urine condensate, a CSF-producing cell culture supernatant or a CSF gene-containing recombinant cell culture supernatant. Such solution is adjusted to pH 6-8 and then either equilibrated with the same buffer as the above-mentioned buffer used in washing the antibody-bound carrier or supplemented with sodium chloride to a concentration of 0.5-1.0 M. The thustreated solution is brought into contact with the antibody-bound carrier. This contact is established in the manner of column chromatography or batchwise chromatography. In the case of column chromatography, the solution is passed through the column at a temperature not exceeding room temperature, preferably at 10° C. or below, at a flow rate of 5-20 ml/cm²/hour, whereby the CSF is adsorbed on the antibody-bound carrier column. It is desirable that the CSF should be adsorbed in an amount of $500-2 \times 10^7$ units per gram (wet weight) of the antibody-bound carrier. After the adsorption treatment, the above-mentioned buffer is passed through the column for washing and removing impurity substances. In the case of batchwise chromatography, the above treated solution is admixed with the antibody-bound carrier at a temperature not exceeding room temperature, preferably at 10° C. or below, and the mixture is stirred for 1-10 hours at such temperature. Thereafter, the antibody-bound carrier is recovered by filtration through a glass filter paper or the like. Said antibody-bound carrier is thoroughly freed from impurity substances by washing with the above-mentioned buffer. The CSF specifically bound to the antibodybound carrier is eluted from the antibody-bound carrier with a dissociating solution for antigen-antibody complexes, for example acetate buffer having a pH of 2-3, 3-4 M thiocyanate solution or 0.1-0.2 M 2,4-dinitrophenol solution. In the case of column chromatography, the CSF is eluted by passing such eluent through the column. In the case of batchwise chromatography, the antibody-bound carrier is suspended in the eluent and the mixture is stirred, whereby the CSF is eluted. The thus-obtained CSF contains no impurities and is a pure form of the CSF.

The CSF according to the invention as produced in the above manner has the physicochemical properties mentioned below. In testing for these physicochemical properties, the CSF purified by the procedure of Reference Example 1 was used.

a) Molecular weight

The molecular weight determined by sodium dodecyl sulfate-polyacrylamide gel electrophoresis in the absence of any reducing agent by the method of Laemmli (Nature, vol. 227, pages 680–685, 1970) was 70,000–90,000 daltons.

Molecular weight determination performed by the same method but following reduction with 0.2 M mercaptoethanol revealed that the CSF had been dissociated into subunits which do not retain biological activity each having a molecular weight of 35,000–45,000 daltons (FIG. 1).

FIG. 1 shows the electrophoretic pattern of the CSF according to the invention as revealed in sodium dodecyl sulfate-polyacrylamide gel electrophoresis. In FIG. 1, A to E each indicates the unreduced form (dimer), F and G each indicates a molecular weight marker protein, and H to L each indicates the reduced form (subunit). The numerical figures on the vertical line indicate molecular weights ($\times 10^3$ daltons).

b) Amino acid sequence of subunit protein

The purified CSF was analyzed for $NH_2$-terminal amino acid sequence in the conventional manner with a vapor-phase amino acid sequencer. The purified CSF was then denatured with 6 M guanidine and alkylated with monoiodoacetic acid and, after desalting, subjected to digestion with trypsin, followed by decomposition with cyanogen bromide. The trypsin-digestion-cyanogen bromide-decomposition product. (peptide mixture) was fractionated by reversed-phase high-performance liquid chromatography using Vydac C-18. The peptide fractions separated were each analyzed with a vapor-phase aminoacid sequencer for determining the amino acid sequence of each peptide fragment. Based on the amino acid sequences of the respective trypsin digestion-cyanogen bromide decomposition product peptide fragments and the base sequence of the mRNA cloned by the present inventors, the primary amino acid structure of the subunit protein was determined. The results of sequencing are as shown in Table 1.

The sequence from the $NH_2$-terminal amino acid (glutamic acid) to the 149th amino acid (glutamic acid) is identical to that of CSF-1, which is a known CSF, but the sequence from the 150th to 214th-238th amino acid (65–89 amino acids) is quite different from that of the known CSF.

As the COO-terminal amino acid, proline was detected as the 214th amino acid, and lysine as the 238th amino acid, depending on the molecular weight of the subunit protein. The 122nd and the 140th amino acid (asparagine) each has a typical N-glycoside binding structure of the formula Asn-X-Ser/Thr (X being an optional amino acid) and it is thought that these sites are the sites of sugar chain binding.

TABLE 1

Subunit amino acid sequence

1
Glu—Glu—Val—Ser—Glu—Tyr—Cys—Ser—His—Met—Ile—Gly—Ser—Gly—His—Leu—Gln—Ser—Leu—Gln—

—Arg—Leu—Ile—Asp—Ser—Gln—Met—Glu—Thr—Ser—Cys—Gln—Ile—Thr—Phe—Glu—Phe—Val—Asp—Gln—

50
—Glu—Gln—Leu—Lys—Asp—Pro—Val—Cys—Tyr—Leu—Lys—Lys—Ala—Phe—Leu—Leu—Val—Gln—Asp—Ile—

—Met—Glu—Asp—Thr—Met—Arg—Phe—Arg—Asp—Asn—Thr—Pro—Asn—Ala—Ile—Ala—Ile—Val—Gln—Leu—

100
—Gln—Glu—Leu—Ser—Leu—Arg—Leu—Lys—Ser—Cys—Phe—Thr—Lys—Asp—Tyr—Glu—Glu—His—Asp—Lys—

—Ala—Cys—Val—Arg—Thr—Phe—Tyr—Glu—Thr—Pro—Leu—Gln—Leu—Leu—Glu—Lys—Val—Lys—Asn—Val—

—Phe—Asn—Glu—Thr—Lys—Asn—Leu—Leu—Asp—Lys—Asp—Trp—Asn—Ile—Phe—Ser—Lys—Asn—Cys—Asn—

150
—Asn—Ser—Phe—Ala—Glu—Cys—Ser—Ser—Gln—Asp—Val—Val—Thr—Lys—Pro—Asp—Cys—Asn—Cys—Leu—

—Tyr—Pro—Lys—Ala—Ile—Pro—Ser—Ser—Asp—Pro—Ala—Ser—Val—Ser—Pro—His—Gln—Pro—Leu—Ala—

200
—Pro—Ser—Met—Ala—Pro—Val—Ala—Gly—Leu—Thr—Trp—Glu—Asp—Ser—Glu—Gly—Thr—Glu—Gly—Ser—

214
—Ser—Leu—Leu—Pro—Gly—Glu—Gln—Pro—Leu—His—Thr—Val—Asp—Pro—Gly—Ser—Ala—Lys—Gln—Arg—

238
—Pro—Pro—Arg—Ser—Thr—Cys—Gln—Ser—Phe—Glu—Pro—Pro—Glu—Thr—Pro—Val—Val—Lys— c) Isoelectric point

The isoelectric point (pI) as determined by the polyacrylamide gel isoelectric focusing and sucrose density gradient isoelectric focusing techniques is 3.1–3.7.

d) Sugar chain-constituting monosaccharides

The constituent monosaccharides contained in the sugar chains bound to the polypeptide were analyzed by high-performance liquid chromatography following hydrolysis for liberation thereof. Aldoses and sialic acids were fractionated on an anion exchange column and hexosamines on a cation exchange column, elution being carried out by the borate buffer concentration gradient elution technique. The constituents were then subjected to post-column labelling with cyanoacetamide or arginine and identified by the fluorescence method. The sugar chains contained in the CSF molecule are variable, hence were difficult to quantitate, although mannose, galactose, N-acetylglucosamine, N-acetylgalactosamine and N-acetylneuraminic acid were identified as constituent monosaccharides.

e) Circular dichroism (CD) spectrum

Figure 2:
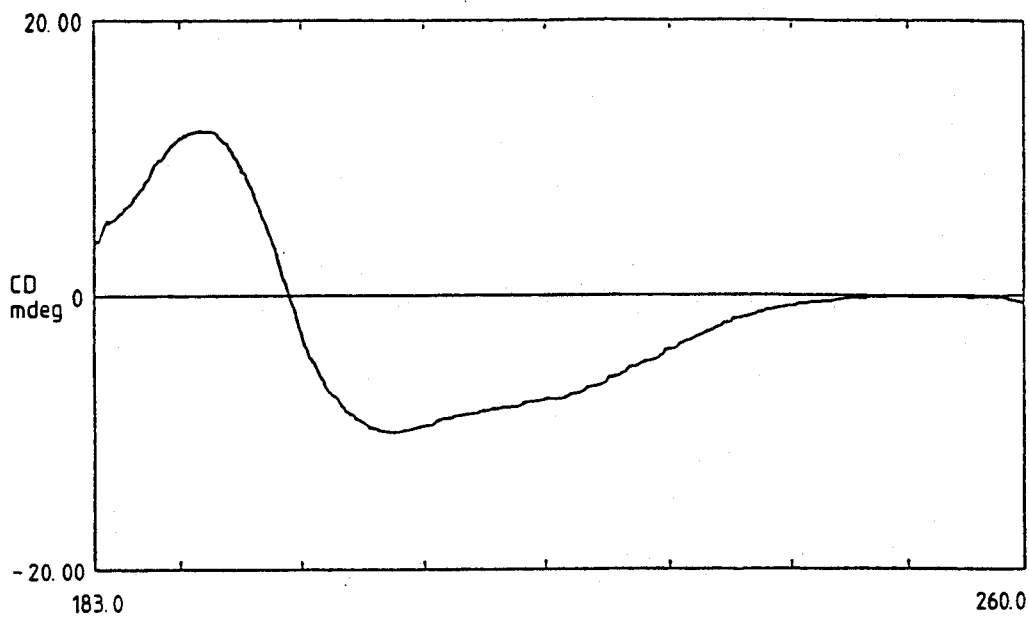
FIG. 2 and FIG. 3 are the far ultraviolet CD spectrum and the infrared absorption spectrum, respectively, of the CSF according to the invention.

The CD spectrum in the far ultraviolet region was measured using a circular dichroism dispersion meter (JASCO model J-600) (FIG. 2).

FIG. 2 shows the CD spectrum of the CSF according to the invention. The wavelength (nm) is on the horizontal axis and the ellipticity (mdeg) on the vertical axis. Minimum peaks are observed at the wavelengths 208 nm and 222 nm. It is therefore estimable that the secondary structure of the CSF contains an α-helix structure.

f) Thermal stability

The CSF was dissolved in a dilute buffer (pH 7.0) to a concentration of 1 μg/ml, and the solution was heated at 60±0.5° C. for 60 minutes and then assayed for colony stimulating activity (to be mentioned later herein). Almost no activity decrease was observed.

g) Infrared absorption spectrum

Figure 3:
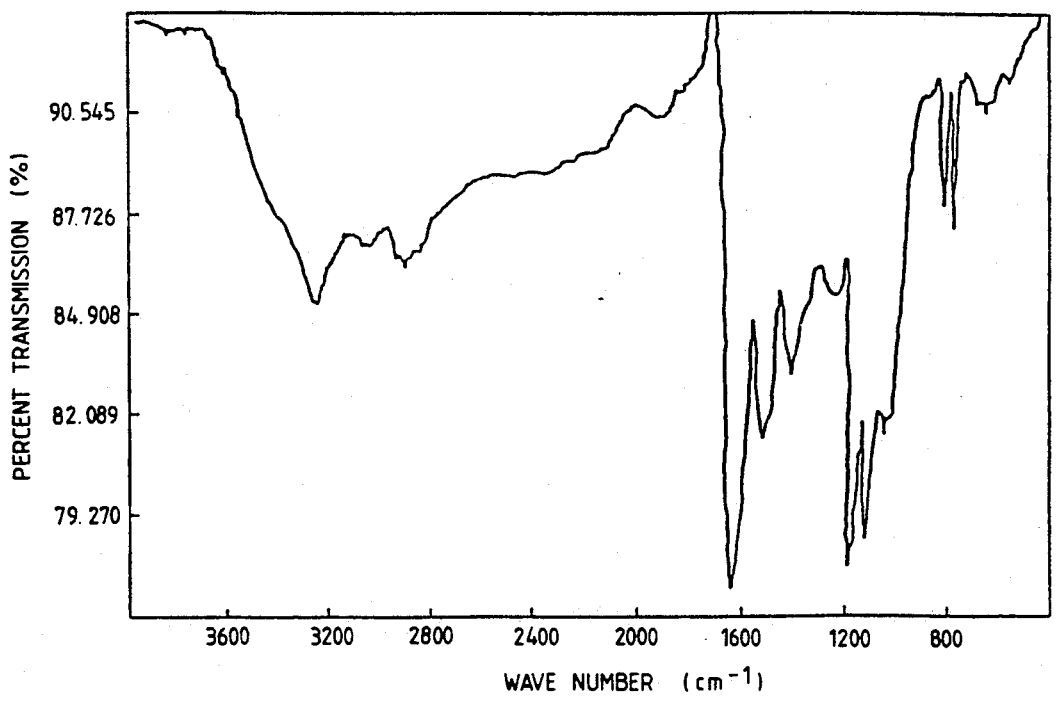

The infrared absorption spectrum of the CSF in the form of a lyophilized powder as recorded by the transmission method (KBr window) using a Fourier-transform infrared spectrophotometer (Nocolet model 5DXC) was as shown in FIG. 3, where the horizontal line is for the wave number ($cm^{-1}$) and the vertical line for the transmittance.

The CSF shows strong absorption at 1650 $cm^{-1}$, 1201 $cm^{-1}$ and 1133 $cm^{-1}$, and medium absorption at 1537 $cm^{-1}$, 1432 $cm^{-1}$ and 1068 $cm^{-1}$.

The glycoprotein having the above physicochemical properties and having colony stimulating activity against mammalian monocyte-macrophage series cells is produced from human urine by either of the above-mentioned production methods or obtained as otherwise disclosed herein, lyophilized in vials under aseptic conditions, and sealed therein in the form of a powder. It is also possible to add an aqueous solution containing human serum albumin (as CSF stabilizer) and an amino acid or sugar (as dissolution aid) to the CSF prior to lyophilization and subject the mixture to sterilization by filtration and then to lyophilization under aseptic conditions.

The colony stimulating activity of the CSF according to the invention was determined by the method involving colony formation of mouse marrow cells on a single-layer soft agar gel. Thus, the CSF sample was admixed with 1 ml of McCoy's 5A medium (GIBCO) containing 0.3% agar, 20% fetal calf serum (FCS) and $1 \times 10^5$ mouse marrow cells. Incubation was carried out at 37° C. for 7 days under a stream of 7.5% $CO_2$-containing air. Thereafter, cell aggregates consisting of 50 or more cells were judged as colonies and counted. The colony stimulating activity was expressed in units. One unit was defined as the quantity of CSF required for the formation of one colony. The specific activity was expressed in terms of the number of colonies (units) formed per milligram of the CSF protein. As a result, the CSF according to the invention was found to have a specific activity of $1.4 \times 10^8$ units per milligram of protein. The colonies formed were stained with hematoxylin-eosin for morphological classification. It was thus found that at least 95% of the colonies formed were monocyte-macrophage colonies.

The preparation according to the invention is administered, for example in the form of a solution in physiological saline, distilled water for injection or the like which has a CSF concentration of 10-100 mg/ml, by intravenous, intramuscular or subcutaneous injection or by intravenous drip. Additives such as albumin, an amino acid (e.g., glycine), sugar (e.g. glucose, sucrose), sugar alcohol (e.g., mannitol), an inorganic salt (e.g., sodium chloride) can be added to the CSF composition.

The dose generally amounts to 1,000-150,000 units/kg body weight per administration once or several times per day but may suitably be increased or decreased depending on the symptom.

It is recommended that the administration of said CSF be started when hemopoietic disorder is expected to begin after chemotherapy or radiotherapy. The administration may be made several times per day over several days (2-14 days) depending on the variation of the blood platelet count until said count returns to a certain constant level.

The target of administration includes all patients with thrombocytopenia induced by hemopoietic disorder, without any particular limitation.

When the preparation according to the invention was administered to such target patients, as described in Clinical Test Examples 1 and 2, marked improvements were observed in the platelet level in the circulating blood. No untoward side effects were observed as resulting from the administration. It is thus suggested that the preparation according to the invention should be useful as a therapeutic agent for thrombocytopenia.

The following test example, examples and reference examples respectively illustrate or demonstrate the toxicity and pharmacological effects of the agent according to the invention and typical methods of production thereof. It is to be noted, however, that these examples are by no means limitative of the scope of the invention.

TEST EXAMPLE 1 (TOXICITY)

The glycoprotein prepared in Reference Example 1 was evaluated for acute toxicity in male $C_{57}BL$ mice by the method of Richard et al. (Journal of Pharmacology and Experimental Therapeutics, vol. 90, page 99, 1949).

The results obtained are shown in Table 2.

TABLE 2

| | $LD_{50}$ |
|---|---|
| Intraperitoneal administration | $1 \times 10^8$ units/kg (4 g/kg) |
| Intravenous administration | $5 \times 10^7$ units/kg (2 g/kg) |
| Subcutaneous administration | $1 \times 10^8$ units/kg (4 g/kg) |

EXAMPLE 1

A malignant tumor patient was subjected to chemotherapy (first chemotherapy), then merely observed for a period (control phase) and, after a second chemotherapy, administered with $8 \times 10^6$ units of a glycoprotein preparation comprising the prepared in Reference Example 1 as active ingredient by intravenous drip for 7 consecutive days (preparation administration phase). Blood granulocytes and platelets were counted at timed intervals. Changes in these parameters are shown in Table 3. The minimum platelet count and the number of days required for the platelet level to regain a level of at least $10^5/mm^3$ in the control phase and in the preparation administration phase are comparatively shown in Table 4.

TABLE 3

| Month/day | Granulocytes (/mm³) | Platelets (/mm³) |
|---|---|---|
| 1/18 | 1,350 | 118,000 |
| 1/21 | 1,380 | 115,000 |
| 1/24 | — | 100,000 |
| 1/27 | 1,020 | 78,000 |
| 1/30 | 200 | 50,000 |
| 2/1 | — | 48,000 |
| 2/2 | 32 | 75,000 |
| 2/4 | 120 | 142,000 |
| 2/6 | 450 | 205,000 |
| 2/9 | 1,400 | 330,000 |
| 2/13 | 1,500 | 350,000 |
| 2/16 | 1,770 | 355,000 |
| 2/19 | 2,380 | 330,000 |
| 2/23 | 2,300 | 320,000 |
| 2/25 | 2,480 | 258,000 |
| 2/27 | 1,720 | 204,000 |
| 3/2 | 1,550 | 105,000 |
| 3/4 | 1,650 | 100,000 |
| 3/6 | 1,600 | 105,000 |
| 3/9 | 1,630 | 135,000 |
| 3/11 | 890 | 190,000 |
| 3/13 | 480 | 270,000 |
| 3/16 | 760 | 320,000 |
| 3/18 | 1,990 | 300,000 |
| 3/20 | 4,800 | 255,000 |

Therapy: Jan. 19 CPA (Cyclophosphamide) 600 mg
ACR (Aclarubicin) 60 mg
CDDP (Cisplatinum) 75 mg
Feb. 23 CPA (Cyclophosphamide) 600 mg
ACR (Aclarubicin) 60 mg
CDDP (Cisplatinum) 75 mg
From February 24, the CSF preparation ( 8 × 10⁶ units/day) was administered once a day for 7 consecutive days.

Note:
the symbol. "—" means "not counted".

TABLE 4

|  | Minimum platelet count | Days required for platelet level to return to 10⁵ |
|---|---|---|
| Control phase | 48,000 | 10 |
| Preparation administration phase | 100,000 | 0 |

EXAMPLE 2

Ten malignant tumor patients were subjected to a first chemotherapy, then observed without any treatment for a period (control phase) and, after a second chemotherapy, administered with $8 \times 10^6$ units of a glycoprotein preparation comprising the CSF prepared in Reference Example 1 as active ingredient by intravenous drip for 7 consecutive days (preparation administration phase). Blood platelets were counted at timed intervals. The minimum platelet count and the number of days required for the platelet count to regain a level of at least $10^5/mm^3$ in the control phase and in the preparation administration phase are comparatively shown in Table 5.

TABLE 5

|  | Minimum platelet count ($\times 10^3/mm^3$) | Days required for platelet level to return to $10^5/mm^3$ |
|---|---|---|
| Control phase | 59.5 ± 30.1 | 7.1 ± 4.8 |
| Preparation administration phase | 119.5 ± 62.6 | 2.5 ± 3.8 |

REFERENCE EXAMPLE 1

Urine (200 liters) collected from healthy humans was adjusted to pH 8.5 with a 10% sodium hydroxide solution, the resultant precipitate was removed by filtration, and the filtrate was concentrated and desalted with an ultrafiltration membrane (Amicon; H10.'.50; cut-off molecular weight: 50,000 daltons). The concentrate was then adjusted to pH 7.0 with a 10% chloric acid solution and heated at 60° C. in a hermetically closed vessel for 10 hours for sterilization. Thereafter the resultant precipitate was removed by centrifugation (5,000×g, 30 minutes), and the supernatant was admixed with DEAE-cellulose equilibrated with 0.02 M phosphate buffer (pH 7.2), for adsorption. Elution was carried out by treating the DEAE-cellulose with 0.02 M phosphate buffer and 0.02 M phosphate buffer (pH 7.2) supplemented with 0.05 M sodium chloride. The eluate was concentrated with an ultrafiltration membrane (Amicon; H1P10) and then subjected to gel filtration using Sephacryl S-300 (Pharmacia, φ4×80 cm) with 0.02 M phosphate buffer (pH 7.2) supplemented with 1 M ammonium sulfate. The fractions corresponding to the molecular weight range of 70,000–150,000 daltons as obtained in the above gel filtration were combined and applied to a phenyl-Sepharose 4B column (Pharmacia, φ2×20 cm) equilibrated with the above-mentioned buffer supplemented with 1 M ammonium sulfate, for adsorption. Elution was carried out with 0.02 M phosphate buffer (pH 7.2) supplemented with 0.5 M ammonium sulfate. The eluate was concentrated with an ultrafiltration membrane (Asahi chemical Industry, NM-3), and the concentrate was subjected to high-performance liquid chromatography using TSKG-3,000SW columns (Tosoh Corporation, φ4×600 mm×2) to give a fraction having the molecular weight range of 70,000–150,000 daltons. This fraction was again concentrated and subjected to highperformance liquid chromatography, which was performed on a reversed-phase Hi-Pore RP-304 (Bio-Rad, φ4×150 mm) column on a linear acetonitrile concentration gradient (0–100%, pH 2.0). The eluent contained 0.1 M trifluoroacetic acid. Thus was eluted a purified CSF, which had a specific activity of $1.4 \times 10^8$ units per milligram of protein. The degree of purification in each step of the above production process was as shown in Table 6.

TABLE 6

| | Purification of CSF | | | |
|---|---|---|---|---|
| Purification step (*) | Protein (mg) | Specific activity (units/mg) | Times purified | Recovery (%) |
| (1) DEAE-cellulose | 733.6 | $1.6 \times 10^5$ | 1 | 100 |
| (2) Sepnacryl S-300 | 149.4 | $5.7 \times 10^5$ | 3.6 | 72.6 |
| (3) Phenyl-Sepharose | 11.3 | $8.8 \times 10^6$ | 55.0 | 85.4 |
| (4) TSKG-3,000 SW | 2.5 | $2.0 \times 10^7$ | 125.0 | 43.6 |
| (5) Hipor-RP-304 | 0.25 | $1.4 \times 10^8$ | 875.0 | 29.9 |

(*) Since untreated human urine contains a CSF-inhibiting substance, accurate activity assay is impossible. Therefore, the activity data are shown only for the DEAE-cellulose treatment step and the subsequent steps

REFERENCE EXAMPLE 2

From 10 rabbits immunized with the CSF obtained in Reference Example 1 and showing a sufficiently increased antibody titer, there was collected an anti-CSF antiserum, which was treated by the above-mentioned method [1] to give about 4 g of a purified anti-CSF antibody. The anti-CSF antibody was dialyzed against 0.1 M phosphate buffer (pH 7.0) and the concentration was adjusted to 20 mg/ml. The antibody solution (200 ml) was added to 100 g of formyl-Cellofine washed in advance with distilled water and with 0.1 M phosphate buffer, the mixture was stirred at room temperature (about 25° C.) for 2 hours, 700 mg of sodium cyanoborohydride was added, and the mixture was stirred for further 16 hours. Thus was prepared an antibody-bound carrier resulting from binding of the anti-CSF antibody to the formyl-Cellofine. The binding product was washed with 0.2 M Tris-hydrochloride buffer (pH 7.0), then 200 ml of Tris buffer containing 500 mg of sodium cyanoborohydride was further added and the mixture was stirred at room temperature for 4 hours for unreacted group inactivation. The antibody-bound carrier was then washed thoroughly with 0.02 M phosphate buffer (pH 7.0) containing 0.5 M sodium chloride. Each gram of the antibody-bound carrier contained 29.5 mg of the anti-CSF antibody bound thereto. Separately, 1,000 liters of urine collected from healthy humans was concentrated and desalted by means of an ultrafiltration concentrator, treated with DEAE-cellulose for active substance adsorption and removal of unadsorbable impurities. Elution was carried out with 0.3 M sodium chloride solution, and sodium chloride was added to the eluate to a concentration of 0.5 M to give a CSF-containing solution. The CSF had a specific activity of $2 \times 10^5$ units/mg. This CSF-containing solution (total volume 500 ml) was added to 100 g of the above-mentioned antibody-bound carrier, and the mixture was stirred overnight (about for 12 hours) at 10° C. or below for batchwise chromatographic treatment. Thereafter, the antibody-bound carrier was recovered by filtration through a glass filter and washed thoroughly with 0.02 M phosphate buffer (pH 7.0) containing 0.5 M sodium chloride. After the washing, 500 ml of 0.2 M acetate buffer (pH 2.5) was added, and the CSF was eluted by stirring the mixture at 10° C. for 1 hour. The eluate was adjusted to pH 7.0 and then concentrated and desalted with an ultrafiltration membrane to give about 10 mg of the CSF in a purified form. The purified CSF had a specific activity of $5.2 \times 10^7$ units/mg and a purity of at least 90% as determined by the SDS-PAGE method.

While the invention has been described in detail and with reference to specific embodiments thereof, it will be apparent to one skilled in the aft that various changes and modifications can be made therein without departing from the spirit and scope thereof.

What is claimed is:

1. A process for preventing thrombocytopenia due to hemopoietic disorder which comprises administering to a patient in need of such prevention a hemopoietic disorder-induced thrombocytopenia effective prevention amount of a human monocyte-macrophage colony stimulating factor.

2. The process according to claim 1 wherein said human monocyte-macrophage colony stimulating factor is composed of two identical subunits and each subunit has the first 214 amino acids of the following amino acid sequence:

1
Glu—Glu—Val—Ser—Glu—Tyr—Cys—Ser—His—Met—Ile—Gly—Ser—Gly—His—Leu—Gln—Ser—Leu—Gln—

—Arg—Leu—Ile—Asp—Ser—Gln—Met—Glu—Thr—Ser—Cys—Gln—Ile—Thr—Phe—Glu—Phe—Val—Asp—Gln—

50
—Glu—Gln—Leu—Lys—Asp—Pro—Val—Cys—Tyr—Leu—Lys—Lys—Ala—Phe—Leu—Leu—Val—Gln—Asp—Ile—

—Met—Glu—Asp—Thr—Met—Arg—Phe—Arg—Asp—Asn—Thr—Pro—Asn—Ala—Ile—Ala—Ile—Val—Gln—Leu—

100
—Gln—Glu—Leu—Ser—Leu—Arg—Leu—Lys—Ser—Cys—Phe—Thr—Lys—Asp—Tyr—Glu—Glu—His—Asp—Lys—

—Ala—Cys—Val—Arg—Thr—Phe—Tyr—Glu—Thr—Pro—Leu—Gln—Leu—Leu—Glu—Lys—Val—Lys—Asn—Val—

—Phe—Asn—Glu—Thr—Lys—Asn—Leu—Leu—Asp—Lys—Asp—Trp—Asn—Ile—Phe—Ser—Lys—Asn—Cys—Asn—

150
—Asn—Ser—Phe—Ala—Glu—Cys—Ser—Ser—Gln—Asp—Val—Val—Thr—Lys—Pro—Asp—Cys—Asn—Cys—Leu—

—Tyr—Pro—Lys—Ala—Ile—Pro—Ser—Ser—Asp—Pro—Ala—Ser—Val—Ser—Pro—His—Gln—Pro—Leu—Ala—

200
—Pro—Ser—Met—Ala—Pro—Val—Ala—Gly—Leu—Thr—Trp—Glu—Asp—Ser—Glu—Gly—Thr—Glu—Gly—Ser—

214
—Ser—Leu—Leu—Pro—Gly—Glu—Gln—Pro—Leu—His—Thr—Val—Asp—Pro—Gly—Ser—Ala—Lys—Gln—Arg—

238
—Pro—Pro—Arg—Ser—Thr—Cys—Gln—Ser—Phe—Glu—Pro—Pro—Glu—Thr—Pro—Val—Val—Lys—.

3. The process according to claim 1 wherein said human monocyte-macrophage colony stimulating factor has the following physicochemical properties a) through f):

a) a homodimer composed of two identical subunits wherein each subunit has a molecular weight of 35,000–45,000 daltons as determined by sodium dodecyl sulfatepolyacrylamide gel electrophoresis, under reducing conditions;

b) a pI of 3.1–3.7 as determined by polyacrylamide gel isoelectric focusing and sucrose density gradient isoelectric focusing techniques;

c) monosaccharide content comprising mannose, galactose, N-acetylglucosamine, N-acetylgalactosamine and N-acetyl-neuraminic acid as determined by high performance liquid chromatography following hydrolysis;

d) a far ultraviolet CD spectrum comprising minimum peaks at the wavelengths 208 and 222 nm as determined with a circular dichroism dispersion meter and having an α-helix structure;
e) is thermally stable even upon heating at α±0.5° C. for 60 minutes; and
f) an infrared absorption spectrum as shown in FIG. 3.

4. A process for treating thrombocytopenia due to hemopoietic disorder which comprises administering to a patient in need of such treatment a hemopoietic disorder-induced thrombocytopenia effective treatment amount of a human monocytemacrophage colony stimulating factor.

5. The process according to claim 4, wherein said human monocyte-macrophage colony stimulating factor is composed of two identical subunits and each subunit has the first 214 amino acids of the following amino acids sequence:

a) a homodimer composed of two identical subunits wherein each subunit has a molecular weight of 35,000–45,000 daltons as determined by sodium dodecyl sulfate-polyacrylamide gel electrophoresis under reducing conditions;
b) a pI of 3.1–3.7 as determined by polyacrylamide gel isoelectric focusing and sucrose density gradient isoelectric focusing techniques;
c) monosaccharide content comprising mannose, galactose, N-acetylglucosamine, Nacetylgalactosamine and N-acetyl-neuraminic acid as determined by high performance liquid chromotography following hydrolysis;
d) a far ultraviolet CD spectrum comprising minimum peaks at the wavelengths 208 and 222 nm as determined with a circular dichroism dispersion meter and having an α-helix structure;

1
Glu—Glu—Val—Ser—Glu—Tyr—Cys—Ser—His—Met—Ile—Gly—Ser—Gly—His—Leu—Gln—Ser—Leu—Gln—

—Arg—Leu—Ile—Asp—Ser—Gln—Met—Glu—Thr—Ser—Cys—Gln—Ile—Thr—Phe—Glu—Phe—Val—Asp—Gln—

50
—Glu—Gln—Leu—Lys—Asp—Pro—Val—Cys—Tyr—Leu—Lys—Lys—Ala—Phe—Leu—Leu—Val—Gln—Asp—Ile—

—Met—Glu—Asp—Thr—Met—Arg—Phe—Arg—Asp—Asn—Thr—Pro—Asn—Ala—Ile—Ala—Ile—Val—Gln—Leu—

100
—Gln—Glu—Leu—Ser—Leu—Arg—Leu—Lys—Ser—Cys—Phe—Thr—Lys—Asp—Tyr—Glu—Glu—His—Asp—Lys—

—Ala—Cys—Val—Arg—Thr—Phe—Tyr—Glu—Thr—Pro—Leu—Gln—Leu—Leu—Glu—Lys—Val—Lys—Asn—Val—

—Phe—Asn—Glu—Thr—Lys—Asn—Leu—Leu—Asp—Lys—Asp—Trp—Asn—Ile—Phe—Ser—Lys—Asn—Cys—Asn—

150
—Asn—Ser—Phe—Ala—Glu—Cys—Ser—Ser—Gln—Asp—Val—Val—Thr—Lys—Pro—Asp—Cys—Asn—Cys—Leu—

—Tyr—Pro—Lys—Ala—Ile—Pro—Ser—Ser—Asp—Pro—Ala—Ser—Val—Ser—Pro—His—Gln—Pro—Leu—Ala—

200
—Pro—Ser—Met—Ala—Pro—Val—Ala—Gly—Leu—Thr—Trp—Glu—Asp—Ser—Glu—Gly—Thr—Glu—Gly—Ser—

214
—Ser—Leu—Leu—Pro—Gly—Glu—Gln—Pro—Leu—His—Thr—Val—Asp—Pro—Gly—Ser—Ala—Lys—Gln—Arg—

238
—Pro—Pro—Arg—Ser—Thr—Cys—Gln—Ser—Phe—Glu—Pro—Pro—Glu—Thr—Pro—Val—Val—Lys—.

6. The process according to claim 4, wherein said human monocyte-macrophage colony stimulating factor has the following physicochemical properties a) through f):

e) is thermally stable even upon heating at 60±0.5° C. for 60 minutes; and
f) an infrared absorption spectrum as shown in FIG. 3.

* * * * *